United States Patent [19]

Campbell et al.

[11] Patent Number: 4,703,017
[45] Date of Patent: Oct. 27, 1987

[54] SOLID PHASE ASSAY WITH VISUAL READOUT

[75] Inventors: Robert L. Campbell, Durham; Daniel B. Wagner, Raleigh; James P. O'Connell, Chapel Hill, all of N.C.

[73] Assignee: Becton Dickinson and Company, Franklin Lakes, N.J.

[21] Appl. No.: 579,667

[22] Filed: Feb. 14, 1984

[51] Int. Cl.$^4$ ................ G01N 33/532; G01N 33/543; G01N 33/544; G01N 33/548
[52] U.S. Cl. .................................. 436/501; 436/518; 436/525; 436/528; 436/530; 436/533; 436/534; 436/800; 436/808; 436/809; 436/815; 436/818; 436/829
[58] Field of Search .............. 422/55, 56, 57, 61; 424/7.1; 435/7, 805, 810; 436/501, 823, 827, 828, 501, 520, 525, 529, 530, 533, 534, 800, 801, 808, 829

[56] References Cited

U.S. PATENT DOCUMENTS

| | | | |
|---|---|---|---|
| 4,169,138 | 9/1979 | Jonsson | 422/57 |
| 4,302,536 | 11/1981 | Longenecker | 435/7 |
| 4,313,734 | 2/1982 | Leuvering | 422/61 |
| 4,373,932 | 2/1983 | Gribnau et al. | 422/61 |
| 4,552,839 | 11/1985 | Gould et al. | 422/56 |
| 4,608,246 | 8/1986 | Bayer et al. | 436/809 |

FOREIGN PATENT DOCUMENTS

| | | | |
|---|---|---|---|
| 8000173 | 8/1981 | Netherlands | 422/61 |
| 80/01515 | 7/1980 | PCT Int'l Appl. | |
| 81/22790 | 10/1981 | PCT Int'l Appl. | |
| 85/01354 | 3/1985 | PCT Int'l Appl. | 435/7 |

OTHER PUBLICATIONS

G. B. Wisdom, *Clinical Chemistry*, 22, 1248–1255, 1976, "Enzyme-Immunoassay".
J. Sharon et al, *Proc. Nat. Acad. Sci., U.S.A.*, 76, 1420–1424, 1979.
T. C. J. Gribnau et al, in T. C. J. Gribnau et al (eds.), *Affinity Chromatography and Related Techniques*, Elsevier Scientific Pub. Co., Amsterdam, 1982, pp. 411–424.
Hawkes et al, "A Dot-Immunobinding Assay for Monoclonal and Other Antibodies", Analytical Biochemistry, vol. 119, pp. 142–147 (1982).
Bennett et al, "An Improved Procedure for the Dot-Immunobinding Analysis of Hybridoma Supernatants", Journal of immunological Methods, vol. 61, pp. 201–207 (1983).
Esen et al, "A Simple and Rapid Dot-Immunobinding Assay for Zein and Other Prolamines", Analytical Biochemistry, vol. 132, pp. 462–467 (1983).
Micheel et al, "A Solid-Phase Immunofluorescence Assay (SIFA) Using Membrane Filters", Acta Histochem, vol. 71, pp. 15–18 (1982).

*Primary Examiner*—Sidney Marantz
*Assistant Examiner*—David A. Saunders
*Attorney, Agent, or Firm*—Elliot M. Olstein

[57] ABSTRACT

Solid phase assay for an analyte wherein binder is supported on a solid support, such as nitrocellulose, and the tracer is comprised of ligand labeled with a colored particulate label, such as a liposome including a dye. The assay has a high sensitivity, and the tracer is visible on the support under assay conditions, whereby tracer can be determined, without instrumentation, and without further treatment thereof.

62 Claims, 1 Drawing Figure

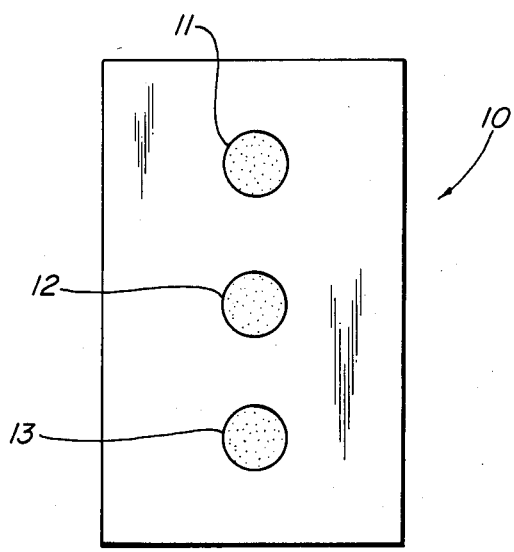

SOLID PHASE ASSAY WITH VISUAL READOUT

This invention relates to an assay for a ligand and to products used in such assay. More particularly, this invention relates to a solid phase assay.

Immunoassay methods, in general, are based on the competition between a specific analyte, the amount of which is to be determined in a sample, and a known amount of tracer, which is generally the analyte or appropriate analog thereof in labeled form, with the analyte and tracer competing for a limited number of available binding sites on a binder which is specific towards the analyte and tracer.

If the concentration of tracer and binder is fixed and the only variable is the level of analyte, it is possible to establish an assay system for measuring the unknown level of analyte by determining the amount of bound and/or free tracer in the system. The values determined in the assay are compared with the values given by a range of known amounts of the analyte treated in the same manner, and by such comparison, it is possible to determine the amount of analyte in the sample.

In one such procedure, the binder is supported on a solid support, whereby the bound and free components of the assay, after incubation, may be easily separated by separation of the sample and the solid support.

In general, the tracers used in such assays require either instrumentation and/or treatment of the tracer in order to determine the tracer in the bound and/or free portion of the assay as a measure of analyte. This, for example, in an assay in which an enzyme is used as the label or marker for the tracer, the enzyme must be developed with a suitable developer. When the label or marker is a fluorescent material, the tracer in the bound and/or free portion is determined by the use of appropriate instrumentation for determining fluorescence.

Thus, there is a need for an assay which would permit determination of an analyte by use of a tracer wherein the tracer can be visually determined without instrumentation and without further treatment of the tracer.

In accordance with one aspect of the present invention, there is provided a method and product for determining analyte wherein a binder for at least one of the analyte and tracer to be used in the assay is supported on a test area located on the surface of a solid support wherein the binder is supported on a test area of the solid support in a concentration whereby the tracer used in the assay, when bound to the binder or to the analyte bound to the binder, under assay conditions, is visible on the support, without further treatment. The tracer used in the assay is a ligand labeled with a particulate label which is visible when bound to the binder on the support or when bound to the analyte bound to the binder on the support, without further treatment, and wherein the ligand is bound by either the binder or analyte.

More particularly, the solid support which is used in the assay is one which has a surface area (area/unit weight of material) such that the binder can be supported on the support in a concentration (weight/unit area) such that the tracer is visible under the assay conditions.

The term "visible" as used herein means that the label can be seen without the use of instrumentation; i.e., with the naked eye.

In accordance with still another aspect of the present invention, there is provided a method and product for determining analytes which are present in test samples in low concentrations wherein the analyte is detected on a test area located on the surface of a solid support by use of a tracer which is visible on the test area, and wherein the solid support has a surface area such that the binder is supported on the test area in a concentration such that the tracer used in the assay is visible on the test area when the analyte is present in the test sample in low concentration. The tracer is a ligand labeled with a particulate label, which is visible when the ligand is bound by either the binder or the analyte.

In accordance with the present invention, the visibility of tracer in the test area (presence and/or absence of visible tracer and/or intensity of visible tracer) is determined as a measure of analyte (presence and/or absence and/or amount of analyte).

The solid support which is employed in the assay is generally a cellulose ester with nitrocellulose giving exceptionally good results. It is to be understood that the term "nitrocellulose" refers to nitric acid esters of cellulose, which may be nitrocellulose alone, or a mixed ester of nitric acid and other acids, and in particular, aliphatic carboxylic acids having from one to seven carbon atoms, with acetic acid being preferred. Such solid supports which are formed from cellulose esterified with nitric acid alone, or a mixture of nitric acid and another acid such as acetic acid, are often referred to as nitrocellulose paper.

Although nitrocellulose is a preferred material for producing the solid support, it is to be understood that other materials, having a surface area sufficient for supporting the binder in a concentration as hereinabove described may also be employed for producing such solid supports.

In general, the support which is used in the assay has a surface area such that it is capable of supporting binder in a concentration of at least 1 $\mu g/cm^2$, (most generally in a concentration of at least 10 $\mu g/cm^2$) and preferably at least 40 $\mu g/cm^2$.

In accordance with a particularly preferred embodiment, the pore size of the solid support is such that the tracer (ligand labeled with a particulate label), when bound to the binder or to the analyte bound to the binder, remains on the surface of the support. Thus, for example, particularly good results have been obtained with a nitrocellulose support having a pore size of from 0.2 to 0.45$\mu$.

Applicant has found that the sensitivity of the assay can be increased by increasing the concentration of binder on the support and, accordingly, supports having high surface areas (such as nitrocellulose) are particularly preferred in that the binder may be supported on such supports in a high concentration. It is to be understood, however, that the concentration of binder which is actually used is dependent in part on the binding affinity of the binder. Accordingly, the scope of the invention is not limited to a particular concentration of binder on the support.

The binder which is supported on the solid support, as hereinabove indicated, is either a binder for both the analyte and tracer, or a binder for only one of the analyte and tracer, with the type of binder which is employed being dependent upon the assay which is to be used for determining the analyte. Thus, for example, if the assay is a competition type of assay, then the binder supported on the solid support would be a binder for both the tracer and analyte, whereby both tracer and analyte would compete for a limited number of binding sites on the binder.

If the assay is a so-called "sandwich" type of assay, then the binder which is supported on the solid support is a binder for only the analyte. In such an assay, the tracer is a tracer which is specific for the analyte, whereby tracer is bound to the analyte which bound to the supported binder.

If the assay is an inhibition type of assay, then the supported binder is specific for only the tracer, and the tracer is also specific for the analyte. In such an assay, the presence of analyte inhibits binding of tracer to the supported binder.

Thus, the tracer when bound to the solid support is either directly bound to the binder on the support or is bound to analyte which is bound to binder on the solid support.

The type of binder which is used in the assay is dependent upon the analyte to be assayed, as well as the specific assay procedure. As known in the art, the binder which is supported may be an antibody including monoclonal antibodies, an antigen, a protein specific for the material to be bound or a naturally occurring binder. Thus, for example, in a competitive type of assay for an antigen or hapten, the binder may be an antibody or a naturally occurring substance which is specific for the tracer and the antigen or hapten. If the assay is for an antibody, then the binder may be, for example, an antigen or an antibody which is specific for the antibody to be assayed. In a "sandwich" type of assay wherein the analyte is an antibody, the supported binder may be an antigen for the antibody, or a protein, such as protein A which selectively binds Fc fragments of certain antibodies. In a "sandwich" type of assay, if the analyte is an antigen (an antigen having more than one determinant site), then the binder may be an antibody or naturally occurring binder which is specific for the antigen to be assayed.

The selection of a suitable binder for support on the solid substrate is deemed to be within the scope of those skilled in the art from the teachings herein.

The ligand which is labeled for use as a tracer in the assay of the present invention is also dependent upon the analyte to be assayed, as well as the assay procedure. Thus, for example, if a competitive assay is employed for determining antigen or hapten, the ligand employed in producing the tracer would be either the analyte or appropriate analog thereof. (The term "appropriate analog" means that the analog of the analyte is bound by the binder for the analyte.)

If the assay is a "sandwich" type of assay for an antibody, then the ligand employed in producing the tracer would be a ligand which is specific for the analyte to be assayed, such as, for example, an antibody elicited in response to the antibody or antigen to be assayed. The selection of a suitable ligand for producing the tracer is deemed to be within the scope of those skilled in the art from the teachings herein.

As hereinabove indicated, in producing the tracer the ligand is labeled with a particulate label, which is visible. A preferred particulate label is a sac, which includes a dye or other colored substance as a marker, whereby the tracer, when used in the assay, is visible without destruction of the sac to release the colored substance.

The sac which is used to label the ligand for producing a tracer may be any one of a wide variety of sacs, including but not limited to intact erythrocytes, erythrocyte ghosts, liposomes (single walled [sometimes called vesicles] or multilamellar), polymer microcapsules (for example, those made by coascervation, or interfacial polymerization), etc.

Erythrocyte ghosts are known in the art and are prepared by suspending erythrocyte cells in a solution of substantially lower osmolarity. The ghosts are "resealed" in an aqueous solution including the marker whereby the ghosts include the marker in the interior thereof. Such procedures are known in the art and the resealing solution of appropriate osmolarity generally includes, in addition to the marker, alkali and alkaline earth metal halides and a coenzyme; e.g., adenosine triphosphate. The preparation of ghosts, as sacs, is disclosed, for example, by D'Orazio et al, *Analytical Chemistry*, Vol. 49, No. 13, pages 2083–86 (November 1977).

Polymer microcapsules are also produced by procedures known in the art except that the solution in which the microcapsules are formed also includes the marker whereby the interior of the polymer microcapsule includes the marker. The preparation of such microcapsules is disclosed for example in *Microencapsulation Processes and Applications*, edited by Jan E. Vandegger (Plenum Press 1974).

As known in the art, liposomes can be prepared from a wide variety of lipids, including phospholipids, glycolipids, steroids, relatively long chain alkyl esters; e.g., alkyl phosphates, fatty acid esters; e.g., lecithin, fatty amines and the like. A mixture of fatty materials may be employed, such as a combination of neutral steroid, a charged amphiphile and a phospholipid. As illustrative examples of phospholipids, there may be mentioned lecithin, sphingomyelin, dipalmitoyl, lecithin, and the like. As representative steroids there may be mentioned cholesterol, cholestanol, lanesterol, and the like. As representative examples of charged amphiphilic compounds, which generally contain from 12 to 30 carbon atoms, there may be mentioned mono- or dialkyl phosphate ester or an alkylamine; e.g., dicetyl phosphate, stearyl amine, hexadecyl amine, dilauryl phosphate, and the like.

The liposome sacs are prepared in an aqueous solution including the marker whereby the sacs will include the marker in the interior thereof. The liposome sacs are easily prepared by vigorous agitation in the solution, followed by removal of marker from the exterior of the sac.

Further details with respect to the preparation of liposomes are set forth in U.S. Pat. No. 4,342,826 and PCT International Publication No. WO80/01515, both of which are hereby incorporated by reference.

As hereinabove indicated, the marker included in the sac is a dye or some other material which is visible, without lysing of the sacs.

The tracer comprised of ligand and particulate label may also be produced by labeling the ligand with an aqueous dispersion of a hydrophobic dye or pigment, or of polymer nuclei coated with such a dye or pigment. Such labels are described in more detail in U.S. Pat. No. 4,373,932, which issued on Feb. 15, 1983. The tracers produced in accordance with such patent may also be employed as tracers in the present invention.

As indicated in the aforesaid patent, the colored organic compounds which are used as labels are in the form of a hydrophobic sol, which hydrophobic organic dyes or pigments are insoluble in water or soluble only to a very limited extent. As indicated in the patent, particles of the aqueous dispersion of a hydrophobic dye or pigment, or of polymeric nuclei coated with such a dye or pigment have a particle size of at least 5 nm, and preferably from 10 to 500 nm.

Such tracers which are labeled with the hydrophobic dye or pigment or with a polymer nuclei coated with such dye or pigment, are visible tracers when used in the assay in accordance with the present invention.

The visible particulate label may be visible polymer particles, such as colored polystyrene particles, preferably of spherical shape.

As representative examples of other particulate labels which may be employed in producing a tracer for use in the assay of the present invention, in which the tracer would be visible, there may be mentioned: ferritin, phycoerythrins or other phycobili-proteins; precipitated or insoluble metals or alloys; fungal, algal, or bacterial pigments or derivatives such as bacterial chlorophylls; plant materials or derivatives, and the like.

The ligand may be labeled with the particulate label so as to produce a tracer for use in the invention by procedures generally known in the art, with the procedure which is used being dependent upon the ligand the the particulate label which is employed. Such techniques include adsorption, covalent coupling, derivatization or activation, and the like. In producing a tracer wherein the ligand is labeled with a sac, the sac may be produced from a component which has been derivatized with a ligand, whereby the sac, when produced, is sensitized with the ligand. In another procedure, the sac including the marker may be initially formed, followed by sensitizing the sac with ligand by procedures known in the art.

Thus, the tracer is comprised of a ligand and a particulate label (solid or solid-like, as opposed to non-solid labels, such as radioisotopes, enzymes and various fluorescent materials), and the particulate label provides a tracer which is visible under the assay conditions so that the presence and/or amount of analyte may be determined without further treatment and without the use of instrumentation; e.g., by use of a liposome containing a dye as the particulate label.

The solid substrate employed in the assay is preferably in sheet form, with the substrate, in sheet form, generally being in the form of a card, a test strip or dipstick, etc. It is to be understood, however, that other forms are also within the spirit and scope of the invention.

The binder is supported on the solid substrate by applying a solution of the binder to a defined area of the test substrate; such as, for example, in the form of a spot, which can be located in a marked area, e.g., square or circle, on the substrate. Particularly good results have been obtained when the binder is applied to the test area as a spot having a diameter of from 3 to 5 mm. The concentration of the binder placed in the defined test area will vary depending upon the assay to be performed; however, ther binder is generally present in a concentration of at least 1 $\mu g/cm^2$ (most generally at least 10 $\mu g/cm^2$), and preferably at least 40 $\mu g/cm^2$. Similarly, the test substrate may contain more than one test area, and each test area may include the same binder, with different affinities and/or in different concentrations, and/or with the same concentration and/or affinity, or the various test areas may include different binders, in which case, the assay may be employed for determining more than one analyte. Although the binder may be appropriately applied to the test substrate for support thereon by adsorption, it is also to be understood that in some cases it may be necessary or desirable to provide for covalent coupling of the binder to the test substrate.

After application of the binder to one or more test areas on the substrate, the residual binding capacity of the test substrate is saturated or blocked by treatment of the test substrate with one or more types of proteins which do not specifically bind the materials to be employed in the assay. Thus, for example, the residual binding capacity of the substrate may be blocked so as to prevent non-specific binding by the use of bovine serum albumin. The techniques for preventing non-specific binding are generally known in the art, and such techniques are also generally applicable to preventing non-specific binding in the assay of the present invention.

The binder supported on the substrate, as hereinabove described, may be employed in an assay for an analyte employing an appropriate tracer as hereinabove described. Thus, for example, in one assay technique useful in determining a hapten or antigen, an antibody is supported on an appropriate test area of the solid substrate; in particular, one formed from nitrocellulose, is contacted and incubated for an appropriate time with a sample containing or suspected of containing analyte. In the preferred embodiment, the antibody is supported on the test area in a concentration such that under the assay conditions, the tracer which is bound to the support is visible over at least a portion of the analyte range of interest. Subsequently, the substrate is washed with buffer, and contacted with tracer, which is preferably the analyte or appropriate analog thereof coupled to a particulate label, preferably a liposome containing a visible dye. The amount of tracer which becomes bound to the supported antibody is inversely proportional to the amount of analyte in the sample. Unbound tracer is rinsed from the substrate, and the presence and/or amount of tracer which remains bound to the substrate may be determined as a measure of the presence and/or amount of analyte present in the sample.

In accordance with the present invention, it is possible to visually determine the presence and/or concentration of tracer on the test substrate without lysing of the liposome. Thus, unlike prior art procedures wherein the detectable marker within the liposome is determined after lysis of the liposome, by proceeding in accordance with the present invention it is possible to determine the tracer on a solid support, without lysis of the liposome.

As an alternative to the above procedure, instead of sequentially adding sample and tracer, the substrate containing the supported antibody may be simultaneously contacted with the analyte to be determined and tracer.

In another type of assay, the "sandwich" technique is employed for determining analyte. In such a technique, the binder supported on a solid support in an appropriate concentration, as hereinabove described, is initially contacted with analyte; for example, antigen. Subsequently, the antigen bound to the binder on the solid support is contacted with tracer, which is, for example, antibody to the analyte labeled with a particulate label, preferably a liposome containing a visible dye. The amount of tracer which is bound to the binder on the solid support through the analyte is directly proportional to the amount of analyte in the sample, and the presence and/or amount of analyte present in the sample may be determined from the presence and/or amount of tracer which becomes bound to the spport through the analyte. As hereinabove described, in accordance with the present invention, it is possible to visually determine the amount of tracer and/or the presence of tracer by use of a sac, including an appropriate dye, as the label, without lysing of the sac.

Assays for various analytes may be readily accomplished in accordance with the present invention by coordinating the amount of binder placed on the test area with other assay parameters so that the analyte can be determined in the range of interest. For example, in one type of assay, using digoxin as a representative analyte, it is possible to use a visible tracer; e.g., digoxigenin coupled to a liposome containing a visible dye, such as rhodamine, to provide a visual semiquantitative assay for digoxin. In particular, a nitrocellulose test card or strip is provided having two test areas, each having a different dilution of antibody to digoxin; e.g. 1:100 and 1:50, with the dilutions and other assay parameters being coordinated in a manner such that when digoxin analyte is present in an amount of 2.0 ng/ml or less, the assay provides a visible color in both test areas (i.e., a digoxin concentration of 2.0 ng/ml or less is not sufficient to inhibit binding of tracer to the binder in an amount such that there is no visible color); when digoxin analyte is present in an amount of greater than 2.0 ng/ml and no greater than 4.0 ng/ml, there is no visible color in the 1:100 dilution test area and a visible color in the 1:50 dilution test area; and when digoxin analyte is present in an amount in excess of 4.0 ng/ml, there is no visible color in either test area.

Although the above type of assay has been described with reference to digoxin, it is to be understood that a similar type of assay could be used with other analytes.

Similarly, by use of a visible tracer as hereinabove described; e.g., ligand labeled with liposome containing a dye, and a nitrocellulose support on which a binder is supported in a test area, by coordinating the affinity of the binder and/or the dilution, with other assay parameters, it is possible to provide a quantitative assay by use of a color chart. For example, binding could be inhibited at a certain analyte concentration (no visible color), and at lower concentrations, the color intensity in the test area would be dependent upon the amount of analyte in the sample; i.e., at increasing concentration, the color is fainter. By use of a color chart prepared by performing the assay with known concentrations of analyte, it is possible to compare the color obtained from assaying a sample containing an unknown amount of analyte with the color chart so as to obtain a reading as to the amount of analyte in the sample.

In another type of assay, a "yes" or "no" answer may be obtained by setting the assay parameters in a manner such that there is no visible color in the test area when the analyte reaches a certain concentration; e.g., the toxicity level of a drug. Such an assay would provide for screening of patients so as to determine whether or not there are toxic levels of a certain drug; e.g., digoxin.

The invention will be further described with respect to the following drawing, wherein:

The drawing is a simplified schematic representation of a preferred test substrate in accordance wth the invention.

Referring now to the drawing, there is shown a test substrate, in the form of a sheet 10, which is formed preferably from nitrocellulose. Sheet 10 includes specified distinct test areas 11, 12 and 13, each of which is provided with binder. For the purposes of describing the test, the binder will be an antibody, and the analyte will be a hapten or antigen. The antibody is applied to test areas 11, 12 and 13, as hereinabove described, and the remainder of the test strip or sheet 10 includes suitable blocking agent to prevent non-specific binding.

The test areas 11, 12 and 13 may be provided with antibodies to the analyte having a different affinity for the analyte, with test area 11 having a high affinity for the analyte, test area 12 a moderate affinity for the analyte, and test area 13 a low affinity for the analyte. Alternatively, test areas 11, 12 and 13 may be provided with antibody having the same affinity for the analyte, with the test area 11 having a high concentration of antibody; test area 12 a medium concentration of antibody; and test area 13 a low concentration of antibody.

The assay protocol and procedure is designed in a manner such that the concentration and/or affinity of the antibody positioned in test areas 11, 12 and 13 are coordinated with the other assay parameters, such as tracer concentration, and the like, to provide a competitive binding assay procedure, so that when the amount of analyte in the sample is below normal (low), there will be a visual readout in all of the test areas 11, 12 and 13; when the amount of analyte is normal there will be a visual readout in only test area 10 or both test area 11 and 12; and when the amount of analyte is above normal (high), there will be a visual readout only in test area 11.

In using test strip 11, the strip may be initially contacted with the sample containing the analyte to be assayed, and after appropriate washing, the test strip 10 is contacted with appropriate tracer, which may be the analyte or appropriate analog thereof coupled to a liposome containing a detectable label, in the form of a visible dye. After washing unbound tracer from the strip 10, by determining the test areas 11, 12 and 13 which are colored, it is possible to determine whether the sample has a high, normal or low concentration of analyte.

Thus, the present invention may be easily adapted to a test strip type of assay which may be easily used as a means of determining analyte in a test sample, wherein such a determination is made by a simple visual readout.

Thus, for example, the test strip may be used in an assay for thyroxine ($T_4$) with the antibody affinity and/or concentration in the test areas 11, 12 and 13 being such that when the $T_4$ concentration is $\geq 12$ $\mu$g/dl (hyperthyroid), the binding of tracer is completely inhibited (no visible color in any of test areas 11, 12 and 13); when the $T_4$ concentration $\geq 8.5$ $\mu$g/dl and $<12$ $\mu$g/dl (euthyroid), the binding of tracer is completely inhibited in areas 12 and 13 and the binding of tracer is not inhibited in area 11 (visible color in only area 11); when the $T_4$ concentration $\geq 5$ $\mu$g/dl and $<8.5$ $\mu$g/dl (euthyroid), the binding of tracer is completely inhibited in area 13 and binding of tracer is not inhibited in areas 11 and 12 (visible color in areas 11 and 12); and when the $T_4$ concentration is $<5$ $\mu$g/dl (hypothyroid) the binding of tracer is not inhibited in any of areas 11, 12 and 13 so as to prevent a visible color (visible color in each of areas 11, 12 and 13).

The present invention may be employed for determining analytes which are generally present in a sample to be assayed in low concentrations. Thus, for example, the present invention may be employed as an assay which provides a visual readout (without instrumentation and/or treatment of the label), with sensitivities for analyte concentrations of $10^{-9}$ gm/ml and less. Thus, the assay of the present invention may be employed as an assay for the analytes which are known to be present in samples of interest in very low concentrations (for example, hcG, digoxin, leutinizing hormone) while retaining the advantage of a visual readout.

Applicant has found that by using a solid support of the type hereinabove described in combination with the hereinabove described tracers and other conditions, it is possible to provide an assay in which the total amount of binder and binder concentration on the support in combination with the tracer provides an assay which is sufficiently sensitive to discriminate between the presence and absence of visual tracer on the support even when the analyte is present in concentrations of $10^{-9}$ gm/ml and less.

In accordance with another aspect of the invention, there is provided a reagent kit or package for accomplishing an assay for an analyte which includes: (a) a solid support having at least one test area, in which a binder for at least one of the analyte and tracer to be used in the assay is supported in a concentration whereby the tracer used in the assay, when bound to the binder on the support or to the analyte bound to the binder on the support, under assay conditions, is visible on the support without further treatment; and (b) a tracer which is a ligand labeled with a particulate label, said tracer being bound by one of the analyte and binder and said particulate label being visible when the tracer is bound without further treatment. In accordance with a preferred embodiment, the solid support is in sheet form and is prepared from nitrocellulose. Although the support is preferably formed of nitrocellulose, other materials having a surface area sufficient for supporting the binder in requisite concentrations may be employed. As hereinabove indicated, the support may include more than one test area, and such plurality of test areas may include the same binder in different concentrations; the same binder having different affinities; or different binders. In accordance with a preferred embodiment, the tracer is labeled sith a sac which includes a visible lable therein, such as a dye, which can be detected without destruction of the sac and without use of instrumentation; i.e., by the unaided eye.

The kit or package may include other components such as standards of the analyte (analyte samples having known concentrations of the analyte), known buffers and the like.

The present invention is applicable to procedures and products for determining a wide variety of analytes. As representative examples of types of analytes, there may be mentioned: drugs, including therapeutic drugs and drugs of abuse; hormones, vitamins, proteins, including antibodies of all classes; peptides; steroids; bacteria; fungi; viruses; parasites; components or products of bacteria, fungi, viruses, or parasites; allergens of all types; products or components of normal or malignant cells; etc. As particular examples, there may be mentioned $T_4$; $T_3$; digoxin; hcG; insulin; theophylline; leutinizing hormone; organisms causing or associated with various disease states, such as streptococcus pyogenes (group A), Herpes Simplex I and II, cytomeglovirus, chlamydiae, etc.

The analyte may be determined in various samples, including for example, body fluids, such as urine, serum, etc. In some cases, it may be possible to detect analyte in whole blood.

As hereinabove indicated, the assay may be qualitative (presence or absence of certain level of analyte) or quantitative or semi-quantitative. The preparation of suitable standards and/or standard curves (the term "standard curve" is used in a generic sense to include a color chart) is deemed to be within the scope of those skilled in the art from the teachings herein.

The present invention is particularly advantageous in that very sensitive assays can be performed with sufficient signal to allow assay results to be determined with the unaided eye (visual readout). It is a further advantage of the assay that the encapsulated marker does not have to be released before results are determined, thereby removing a step and simplifying the assay. In addition, the assay can be rapidly performed.

The present assay is as sensitive as radioassays, yet does not have the disadvantages which are inherent in a radioassay. It was completely unexpected that there could be provided a visual readout with such sensitives without the use of instrumentation and/or further steps to develop the label portion of the tracer.

Because of the overall simplicity of the assay to the end user, the assay can be readily performed by untrained persons. The solid phase, once prepared, should be stable for long periods of time. Minor errors in sample volume added or in volume of tracer added do not significantly affect the assay results. The assay described herein is sufficiently simple and reliable even for use in the home, and in this case, has sufficient sensitivity to detect a wide variety of analytes not commonly available in a simple test format.

Thus, for example, as a result of its sensitivity, an hCG assay perfomed in accordance with the present invention can detect pregnancy in its early stages. Moreover, such a test can be easily adopted to home use as a result of its simplicity.

Particularly good results (high sensitivity) are obtained when the particulate label is a liposome; however, the scope of the invention is not limited to liposomes.

The invention will be further described with respect to the following examples; however, the scope of the invention is not to be limited thereby:

EXAMPLE I

LIPOSOME PREPARATION

1. To a 100 ml round-bottom rotoevaporator flask, add the following:
   a. 48 mg cholesterol, Sigma #CH-S
   b. 104 mg distearoyl phosphatidyl choline (DSPC), Avanti Polar Lipids #850365 (20 mg/ml in $CHCl_3$)
   c. 3.75 mg crosslink agent (distearoyl phosphatidyl ethanolamine-(p-maleimidophenyl)butyrate (DSPE-MPB) prepared in-house, 2 mg/ml in $CHCl_3$ as described in Example IA.)
   d. 6.0 ml isopropyl ether, Fisher #E-141
   e. 1.0 ml methanol, Aldrich #15,490-3
2. Swirl to mix.
3. Add 5.0 ml 0.1M Sulforhodamine B, Eastman #14321, prepared in 0.1M sodium acetate/0.1M NaCl, pH 4.5 buffer.
4. Swirl to mix.
5. Flush vessel with $N_2$.
6. Sonicate in room temperature, water bath sonicator for 10 min in order to emulsify.
7. Place on rotoevaporator with the following settings: Water bath temperature=44° C. Rotation speed=4.
8. Slowly increase vacuum until foaming ceases (approximately 30–40 min).

9. Reduce pressure and allow liposomes to anneal at 44° C. for 30 min.
10. Add 10 ml of warm (50°–52° C.) 0.1 molar sulforhodamine B to vessel and mix.
11. Extrude the warm liposome preparation through a 0.4 micron then a 0.2 micron Biorad Unipore polycarbonate membrane (Biorad #313-0059 and #313-5059, respectively).
12. Dilute liposomes to a total volume of approximately 80 ml in a 90 ml ultracentrifuge tube using sodium acetate/saline buffer, pH 4.5.
13. Centrifuge at 75,000 Xg for 30 min.
14. Resuspend pelleted liposomes to 80 ml with sodium acetate/saline buffer, pH 4.5.
15. Repeat #13 and #14, then #13 again.
16. Resuspend pelleted liposomes in 10 ml Tris buffer, pH 8.0 (50 mM Tris, 100 mM NaCl, 1 mM EDTA, 310 mOs/kg).
17. Hold at 4° C. until protein reaction.

EXAMPLE IA

PREPARATION OF DISTEAROYLPHOSPHATIDYLE-THANOLAMINEMALEIMIDOPHENYLBUTY-RATE USED IN EXAMPLE I

Distearoylphosphatidylethanolamine (119.2 mg, 0.1593 mmol, Avanti Polar Lipid) was suspended in 30 ml of chloroform and heated to reflux under a nitrogen atmosphere until all solid had dissolved. The solution was allowed to cool to room temperature followed by the addition of triethylamine (22.2 ul, 0.1593 mmol, Aldrich) and succinimidyl-4-(p-maleimidophenyl)butyrate (79.45 mg, 0.2230 mmol, Pierce). The reaction mixture was allowed to stir overnight at room temperature under a nitrogen atmosphere. The mixture was concentrated under reduced pressure to yield a pale yellow waxy solid (270.7 mg) that appeared as one major spot and several minor spots upon tlc analysis (silica, 65:25:4 $CH_2Cl_2$:$CH_3OH$:$H_2O$). The spot was visualized with UV light and Molybdenum Blue Spray Reagent (Sigma), $R_f$ 0.5

The crude product was chromatographed on four silica gel, preparative, thick-layer plates (E. Merck, 2.0 mm) developing with 65:25:4 $CH_2Cl_2$:$CH_3OH$:$H_2O$. The upper band of the two Molybdenum Blue active bands was isolated and the product extracted with 50% $CH_2Cl_2$:$C_2H_5OH$. Evaporation of the solvent afforded the product as a white solid (65.75 mg).

IR (neat): 2910(s), 2845(s), 1734(s), 1715(s), 1510(m), 1460(m), 1390(m), 1370(mw), 1242(m), 1230(m), 1100(m), 1060(m), 905(m), 820(m), 685 $cm^{-1}$(m).

The liposomes prepared in this manner include rhodamine dye and may be sensitized with a ligand by procedures known in the art to produce a tracer for use in the present invention.

The following Example II illustrates the preparation of tracer by sensitizing the liposome with an antibody.

SENSITIZING LIPOSOME (EXAMPLE I) WITH ANTIBODY TO PRODUCE TRACER

EXAMPLE II

1. To 8 mg protein A purified antibody, add 0.4 ml 1M dithiothreitol in sodium acetate/saline buffer, pH 4.5.
2. Vortex and let react 30 min at room temperature in the dark.
3. Remove dithiothreitol by passing the reaction volume over a Sephadex G-25 medium column equilibrated with Tris ph 8.0 buffer (50 mM Tris, 100 mM saline, 1 mM EDTA, 310 mOs/kg).
4. Monitor the O.D. 280 and pool void volume fractions.
5. Mix this solution with the 10 ml of freshly prepared liposomes.
6. Flush with $N_2$ and seal.
7. React overnight at room temperature.
8. Wash twice, by centrifugation, these protein-labeled liposomes using the standard Tris buffer.
9. After last wash, resuspend pellet in 40 ml Tris.
10. Store at 4° C.

EXAMPLE III

NITROCELLULOSE DISC IMMUNOASSAY FOR HCG (PREGNANCY TEST)

REAGENTS:
1. Adsorption Buffer 5: BD, Catalog #614335
2. HCG antibody to the alpha-chain of hcG
3. Nitrocellulose Paper: Schliecher & Schuill, ME 25, 0.45 um porosity
4. Bovine Serum Albumin: Sigma, Catalog #A-7906
5. Urine Controls: BDI, Catalog #255815
6. Tracer: Liposome prepared by method of Example I and sensitized with antibody to the beta chain of hcG by the method of Example II.

PROCEDURE:
1. Cut 1 cm disc of nitrocellulose paper.
2. Pipet 3 ul of 1:50 dilution of HCG antibody (dilution made in AB5) to the center of disc.
3. Allow to dry at room temperature 15 minutes.
4. Pipet 300 ul of 5% BSA in AB5 (filtered through 0.45 micron filter prior to use) to each disc.
5. Incubate disc 1 hour at 37° C.
6. Decant liquid.
7. Pipet 200 ul of urine control or urine.
8. Incubate 1 hour at room temperature.
9. Decant control or urine.
10. Wash disc twice with 1.5 ml AB5.
11. Pipet 300 ul of 1:12 dilution of tracer (dilution made in AB5) to each disc (stock liposomes contain about 1$\mu$ mole lipid/ml)
12. Incubate 1 hour at room temperature.
13. Decant tracer.
14. Wash twice with 1.5 ml AB5.
15. Visible spot is positive for pregnancy.

| | Qualitative Urine RIA Results Vs. Nitrocellulose Disc Test Results | | |
|---|---|---|---|
| Urine Number | Gestation Period | RIA Results | Spot Test |
| 1 | 11 wk | Pos | Pos |
| 2 | 10 wk | Pos | Pos |
| 3 | 7½ wk | Pos | Pos |
| 4 | 8½ wk | Pos | Pos |
| 5 | 11¼ wk | Pos | Pos |
| 6 | 11½ wk | Pos | Pos |
| 7 | 9 wk | Pos | Pos |
| 8 | 8½ wk | Pos | Pos |
| 9 | 10 wk | Pos | Pos |
| 10 | 8½–12 wk | Pos | Pos |
| 11 | None | Borderline | Neg |
| 12 | None | Neg | Neg |
| 13 | None | Neg | Neg |
| 14 | None | Neg | Neg |

RIA done by BD HCG $I^{125}$ kit.
Urines obtained from clinical physician's office

EXAMPLE IV

In this example, the liposomes are replaced by dyed plastic latex particles.

Tetanus immune globulin (Human, Wyeth Laboratories) was diluted to 10 units/ml in 0.1M borate buffer (pH 9) containing 0.06M NaCl. Five microliters of the antibody solution was spotted onto the surface of a small (~1 cm diameter) circle of nitrocellulose paper (Schiecher and Schill), BA 85/5, 0.45u pore size, and allowed to dry for 30 minutes. The disc was immersed in a 2% solution of Bovine serum albumin in ARIA Adsorption Buffer #5 (BDAI, Salt Lake City, Utah, Cat. #614335) for about 30 minutes and dried.

Control paper was prepared as described, except that the tetanus immune globulin was omitted.

Dyed red polystyrene latex particles (Polysciences, Inc. Cat. #15708, Lot 12460, 0.55u diameter) were washed several times with 0.1M borate, 0.06M NaCl buffer by centrifugation (13000 x G, 5 min.), and sensitized with 600 Lf/ml of tetanus toxoid (obtained from the Massachusettes Department of Health) in 0.1M borate buffer for 4 days at 4° C. The sensitized particles were washed several times with buffer, and stored as a 1% solution by weight.

The test demonstrating immunoreactivity was run as follows:

Control and antibody-coated paper discs were placed into individual wells on a Falcon ® 3047 24-well tissue culture plate. 400 ul of 0.1M borate buffer was added to 200 ul of the stock sensitized latex particles, and 300 ul of this suspension was added to the wells into which the prepared nitrocellulose were placed. The plate was incubated at room temperature for 1 hour, after which the paper discs were removed and rinsed briefly with buffer solution. The disc containing specific antibody contained a clearly visible spot of colored latex particles whereas the control paper showed no such spot, indicating that an immunological reaction had taken place. These results were confirmed with a scanning electron microscope.

EXAMPLE V

PREPARATION OF DISTEAROYLPHOSPHATIDYLETHANOLAMINE-DIGLOXIGENIN

Distearoylphosphatidylethanolamine (400.0 mg, 0.5346 mmol, Avanti Polar Lipid) was suspended in 50 ml of $CHCl_3:CH_3OH$ (9:1) and heated to reflux under a nitrogen atmosphere until all solid had dissolved. The solution was allowed to cool followed by the addition of 3-ketodigoxigenin (207.7 mg, 0.5346 mmol) ad 2.0 g of 4A sieves (Sigma). The reaction mixture was allowed to stir at 60° C. for 3 hr under a nitrogen atmosphere at which time sodium cyanoborohydride (39.95 mg, 0.5881 mmol, Sigma) was added. The mixture was then allowed to stir at room temperature overnight. The reaction was filtered and concentrated under reduced pressure to yield a white foam (579.6 mg) that appeared as one major spot and several minor spots under tlc analysis (silica, 20% $CH_3OH:CH_2Cl_2$). The spot was visualized by Phosphomolybdic Acid Spray Reagent (Sigma), $R_f$ 0.3.

The crude product was purified by low pressure column chromatography (silica gel, 10% $CH_3OH-CH_2Cl_2$) to yield the product as a white solid (185.3 mg). The product was detected by a variable wavelength UV detector set at 230 nm.

EXAMPLE VI

PREPARATION OF LIPOSOME CONTAINING RHODAMINE DYE SENSITIZED WITH DIGOXIGENIN (TRACER)

Phosphatidyl choline, dipalmitoyl (dppc), cholesterol (chol), phosphatidyl ethanolamine, distearoyl-digoxigenin (dspe-dig) (Example V), and phosphatidyl glycerol, dipalmitoyl (dppG) are dissolved in chloroform/methanol (20:1) in the ratio of 50 mole % chol, 40 mole % dppc, 10 mole % dppg and a trace amount (e.g., 200 ug) of dspe-dig is added. The lipids are dried on the inside of a round bottom flask under reduced pressure on a rotary evaporator, and subsequently placed on a lyophilizer overnight to remove all traces of residual solvent. A solution of 0.1M sulforhodamine B in water is added to the flask (10 ml), and the flask is shaken vigorously or, if desired, sonicated briefly. This operation is conducted at 60° C. The liposomes form spontaneously under this condition as it is known in the art, and contain approximately 0.1M rhodamine dye encapsulated. Detectable digoxigenin is exposed on the surface of the liposomes. The liposomes are washed several times in a buffer solution of the same osmolarity as the encapsulated dye (about 310 mosm/Kg) to prevent osmotic lysis. The preparation is filtered through a 0.4 or 0.2u filter to remove the larger liposomes. The liposomes are diluted in buffer solution so as to contain 1u mole of phospholipid per ml of buffer solution.

EXAMPLE VII

DIGOXIN PROCEDURE

Paper Spotting Procedure:
1. Spot nitrocellulose paper (ME-25) dots with 5 ul of rabbit anti-digoxin antibody in Tris buffer containing 0.1% BSA, [6.005 gm Tris base, 0.358 gm EDTA trisodium, 6.83 gm NaCl, 0.2 gm $NaN_3$, 1 gm BSA q.s. to 1 L with HPLC water, pH to 8.0 with HCl. Adjust to 310 mOs/kg using a 4M NaCl solution at various concentrations which demonstrate inhibition. Let air dry for 30 minutes.
2. Cover the nitrocellulose paper dots with 300 ul of 3% BSA in Tris buffer [6.055 gm Tris base, 0.358 gm EDTA trisodium, 6.83 gm NaCl, 0.2 gm $NaN_3$, 30 gm BSA q.s. to 1 liter with HPLC water, pH to 8.0 with HCl. Adjust to 310 mOs/kg using 4M NaCl solution. Let dots soak in BSA for 30 min to 1 hr or until the dot is completely saturated. After saturation, remove BSA either by decantation or by aspiration.

Assay Procedure:
1. Cover pretreated dots with digoxin standards [0 ng/ml; 0.5 ng/ml; 1.0 ng/ml; 2.5 ng/ml] and/or patient serums. Let dot soak in standards and/or serums for 10 minutes. Remove standards and/or patient serums by either decantation or aspiration. After removing standards and/or patient serums, wash dots twice with Tris buffer [6.005 gm Tris base, 0.358 gm EDTA trisodium, 6.83, gm NaCl, 0.2 gm $NaN_3$, q.s. to 1 liter with HPLC water, pH to 8.0 with HCl. Adjust to 310 mOs/kg using NaCl solution.
2. Cover dots with 500 ul of sensitized liposomes (containing 100–400 ug PE-digoxigenin of Example VI which have been diluted in Tris buffer [6.055 gm Tris base, 0.358 gm EDTA trisodium 6.83 gm NaCl, 0.2 gm $NaN_3$, q.s. to 1 L with HPLC water, pH to 8.0 with HCl. Adjust to 310 mOs/kg using 4M NaCl solution at a dilution that demonstrates inhibition. Let dot soak in the liposomes for 15 minutes. Remove liposomes by either decantation or aspiration. After removing liposomes, wash dots twice with Tris buffer [6.055 gm Tris base, 0.358 gm EDTA trisodium, 6.83 gm NaCl, 0.2 gm NaN$_3$ q.s. to 1 L with HPLC water, pH to 8.0 with HCl. Adjust to 310 mOs/kg using 4M NaCl solution.

Assay Interpretation:

1. For the purposes of this study, the antibody dilutions used were 1:200, 1:1200, and 1:2200. These dilutions may vary. The results are as follows:

At the 1:200 dilution pink dots were obtained at all standard concentrations. This dilution is used as a reference only.

At the 1:1200 dilution pink dots were obtained at the 0 ng/ml, 0.5 ng/ml, and 1.0 ng/ml standard concentrations. There was no pink dot at the 2.5 ng/ml standard concentration showing that when 2.5 ng/ml of digoxin or higher is present, no color would be visible.

At the 1:2200 dilution pink dots were obtained at the 0 ng/ml, 0.5 ng/ml standard concentrations. There were no pink dots at the 1.0 ng/ml and 2.5 ng/ml standard concentrations showing that when 1.0 ng/ml of digoxin or higher is present, no color would be visible.

For Patient Serum Determinations:

Ten patient serums were set up as previously described, and the results were compared to the following key:

|  | Color | No Color |
| --- | --- | --- |
| At the 1:200 dilution | If patient serum is less than 2.5 ng/ml | If patient serum is greater than 2.5 ng/ml |
| At the 1:2200 dilution | If patient serum is less than 1.0 ng/ml | If patient serum is greater than 1.0 ng/ml |

Using this format, nine out of ten patient serum value ranges (i.e., greater than 2.5 ng/ml; within 1.0–2.5 ng/ml range; or less than 1.0 ng/ml) were determined accurately.

Although the assay and product of the present invention are capable of determining analyte by determining tracer without instrumentation, it is to be understood that the scope of the invention and claims is not limited to such a determination in that, as should be apparent, although the tracer is visible, a user of the assay could elect to use instrumentation in making the determination. Similarly, although the tracer may be determined without lysis or destruction of the sac containing the visible marker; in particular, a visible dye, it is to be understood that the scope of the invention and claims is not limited to such a determination in that, as should be apparent, a user of the assay could elect to destroy the sac before making the determination.

Numerous modifications and variations of the present invention are possible in light of the above teachings and, therefore, within the scope of the claims the invention may be practiced otherwise than as particularly described.

What is claimed is:

1. A process for assaying for an analyte, comprising:
contacting a binder supported on a test area of a solid support with a solution of analyte and a tracer, said binder being a binder for at least the analyte, said tracer being comprised of a ligand labeled with a visible particulate label wherein when said particulate label is a sac including a visable dye, said sac is selected from the group consisting of liposomes and microcapsules, said ligand being bound to one of the binder and analyte whereby the tracer is bound to one of the binder on the support and the analyte bound to the binder on the support, said test area being formed of a material having a surface area for supporting the binder and the binder being supported in a concentration whereby bound tracer is visible on the support under assay conditions, said binder being supported in a concentration of at least 1 $\mu$g/cm$^2$; and determining the visibility of tracer bound in said test area as a measure of analyte in a sample.

2. The process of claim 1 wherein analyte and tracer are sequentially contacted with the binder on the solid support.

3. The process of claim 1 wherein the analyte and tracer are simultaneously contacted with binder on the solid support.

4. The process of claim 1 wherein the label of the tracer is a sac including a visible dye.

5. The process of claim 4 wherein the sac is a liposome.

6. The process of claim 5 wherein the visibility of the bound tracer is determined without lysis of the liposome.

7. The process of claim 1 wherein the solid support is in sheet form.

8. The process of claim 1 wherein the binder is an antibody.

9. The process of claim 8 wherein the tracer is a labeled form of the analyte.

10. The process of claim 8 wherein the tracer is a labeled form of an antibody for the analyte.

11. The process of claim 1 wherein the analyte is digoxin.

12. The process of claim 1 wherein the analyte is hCG.

13. The process of claim 1 wherein the particulate label is a colored particle.

14. A process for assaying for an analyte, comprising:
contacting a binder supported on a test area of a solid support with a solution analyte and a tracer, said binder being a binder for at least the analyte, said tracer being comprised of a ligand labeled with a visible particulate label wherein when said particulate label is a sac including a visible dye, said sac is selected from the group consisting of liposomes and microcapsules, said ligand being bound by one of the binder on the support and the analyte bound to the binder on the support, said test area being formed of nitrocellulose, said binder being supported in said test area in a concentration whereby bound tracer is visible on the support under assay conditions, said binder being supported in a concentration of at least 1 $\mu$g/cm$^2$; and determining the visibility of tracer bound in said test area as a measure of analyte in a sample.

15. The process of claim 14 wherein the visible particulate label is a sac including a visible dye.

16. The process of claim 15 wherein the sac is a liposome.

17. The process of claim 16 wherein the visibility of tracer in said test area is determined without lysis of the liposome.

18. The process of claim 17 wherein the analyte is hCG.

19. The process of claim 17 wherein the analyte is digoxin.

20. The process of claim 17 wherein the analyte is in a sample in a concentration of no greater than $10^{-9}$ gm/ml.

21. The process of claim 14 wherein the analyte is in a sample in a concentration of no greater than $10^{-9}$ gm/ml.

22. The process of claim 14 wherein the solid support is in sheet form.

23. The process of claim 14 wherein the support contains a plurality of said test areas.

24. The process of claim 14 wherein the particulate label is a colored particle.

25. The process of claim 14 wherein the particulate label is a hydrophobic dye.

26. The process of claim 14 wherein the binder is supported in a concentration of at least 40 $\mu g/cm^2$.

27. The process of claim 26 wherein the binder is in the test area as a spot having a diameter of from 3 to 5 mm.

28. The process of claim 1 wherein the assay is for hCG, the binder is antibody to hCG and said tracer is comprised of antibody to hCG labeled with a colored particulate label.

29. The process of claim 28 wherein the test area is formed of nitrocellulose.

30. The process of claim 29 wherein the particulate label is a sac.

31. The process of claim 30 wherein the particulate label is a sac containing a visible dye and visibility is determined without lysis of the sac.

32. The process of claim 31 wherein the particulate label is a liposome containing rhodamine.

33. The process of claim 1 wherein the assay is for digoxin said binder is antibody to digoxin and the tracer is comprised of an analogue of digoxin bound by said antibody labeled with a colored particulate label.

34. The process of claim 33 wherein the test area is formed of nitrocellulose.

35. The process of claim 34 wherein the particulate label is a sac.

36. The process of claim 35 wherein the particulate label is a sac containing a visible dye and visibility is determined without lysis of the sac.

37. The process of claim 36 wherein the particulate label is a liposome containing rhodamine.

38. A reagent kit for determining an analyte in solution comprising:
a solid support including a binder on a test area of the solid support in a concentration of at least 1 $\mu g/cm^2$; and a tracer, said binder being a binder for at least the analyte, said tracer being comprised of a ligand labeled with a visible particulate label wherein when said particulate label is a sac including a visible dye, said sac is selected from the group consisting of liposomes and microcapsules, said ligand being bound to one of the binder on the support and the analyte bound to the binder on the support during an assay, said test area being formed of a material having a surface area for supporting the binder and the binder being supported in a concentration whereby bound tracer is visible on the support under assay condition, said binder being supported in a concentration of at least 1 $\mu g/cm^2$.

39. The kit of claim 38 wherein the test area is formed of nitrocellulose.

40. The kit of claim 39 wherein the binder is an antibody.

41. The kit of claim 40 wherein the label of the tracer is a lipsome including a visible dye.

42. The kit of claim 41 wherein the analyte is hCG.

43. The kit of claim 42 wherein the binder is antibody to hCG and the ligand of the tracer is antibody to hCG.

44. The kit of claim 41 wherein the analyte is digoxin, the binder is antibody to digoxin and the ligand of the tracer is an analogue of digoxin.

45. The kit of claim 39 wherein the label of the tracer is a liposome including a visible dye.

46. The process of claim 1 wherein the analyte is present in a concentration of no greater than $10^{-9}$ grams per milliliter.

47. The process of claim 1 wherein said test area is capable of supporting binder in a concentration of at least ten micrograms per centimeter.

48. The process of claim 46 or 47 wherein the binder is in the test area as a spot.

49. The process of any one of claims 1, 46 or 48 wherein the particulate label is a precipitated or insoluble metal or metal alloy.

50. The process of claim 46 wherein the label of the tracer is a liposome including a visible dye.

51. The process of claim 14 or 21 wherein the particulate label is a precipitated or insoluble metal or metal alloy.

52. The kit of claim 38, 39 or 40 wherein the binder is in the test area as a spot.

53. The kit of claim 38, 39 or 40 wherein the particulate label is a precipitated or insoluble metal or metal alloy.

54. The process of claim 14 wherein the ligand is bound to the analyte whereby the tracer is bound to the analyte.

55. The process of claim 54 wherein ligand is directly bound to the analyte whereby the tracer is directly bound to the analyte.

56. The process of claim 1 wherein the ligand is bound to the analyte whereby the tracer is bound to the analyte.

57. The process of claim 56 wherein ligand is directly bound to the analyte whereby the tracer is directly bound to the analyte.

58. The process of claim 5 or 16 wherein the visible dye is sulforhodamine B.

59. A process for assaying for an analyte, comprising:
contacting a binder for an analyte supported on a test area of a solid support with a solution of analyte to bind analyte to said binder;
determining bound analyte by use of a tracer comprised of a ligand labeled with a visible particulate label wherein when said particulate label is a sac including a visible dye said sac is selected from the group consisting of liposomes and microcapsules, said test area being formed of a material having a surface area for supporting the binder and the binder being supported in a concentration whereby tracer is visible on the support under assay conditions, said binder being supported in a concentration of at least 1 $\mu g/cm^2$, said analyte being determined by the visibility of the tracer in the test area.

60. The process of claim 59 wherein the test area is formed from nitrocellulose.

61. The process of claim 59 wherein the particulate label is a liposome including a visible dye.

62. The process of any one of claims 59, 60 or 61 wherein the binder is supported in a concentration of at least 10 ug/cm.

* * * * *

(12) REEXAMINATION CERTIFICATE (4497th)
United States Patent
Campbell et al.

(10) Number: US 4,703,017 C1
(45) Certificate Issued: Dec. 4, 2001

(54) SOLID PHASE ASSAY WITH VISUAL READOUT

(75) Inventors: Robert L. Campbell, Durham; Daniel B. Wagner, Raleigh; James P. O'Connell, Chapel Hill, all of NC (US)

(73) Assignee: Becton, Dickinson and Company

Reexamination Request:
No. 90/005,656, Mar. 1, 2000

Reexamination Certificate for:
Patent No.: 4,703,017
Issued: Oct. 27, 1987
Appl. No.: 06/579,667
Filed: Feb. 14, 1984

(51) Int. Cl.[7] ............... G01N 33/532; G01N 33/543; G01N 33/544; G01N 33/548
(52) U.S. Cl. ............... 436/501; 436/518; 436/525; 436/528; 436/530; 436/533; 436/534; 436/800; 436/808; 436/809; 436/815; 436/818; 436/829; 435/7.1; 435/287.7; 422/55; 422/56
(58) Field of Search ............... 422/55, 56, 57, 422/61; 435/7.1, 805, 810; 436/501, 518, 525, 529, 530, 533, 534, 800, 801, 808, 809

(56) References Cited

U.S. PATENT DOCUMENTS

| | | |
|---|---|---|
| 3,641,235 | 2/1972 | Weiss ................................ 424/8 |
| 3,666,421 | 5/1972 | Price ................................ 23/253 |
| 3,859,430 | 1/1975 | Parikh et al. ........................ 424/1 |
| 3,868,219 | 2/1975 | Hurenkamp ...................... 23/230 B |
| 3,876,504 | 4/1975 | Koffler .......................... 195/103.5 R |
| 4,002,532 | 1/1977 | Weltman et al. ............ 195/103.5 A |
| 4,036,946 | 7/1977 | Kleinerman ...................... 424/8 |
| 4,038,485 | 7/1977 | Johnston et al. ............... 23/230 B |
| 4,067,959 | 1/1978 | Bolz ................................ 424/1 |
| 4,071,315 | 1/1978 | Chateau ........................ 23/230 B |
| 4,092,408 | 5/1978 | Litt ................................ 424/1 |
| 4,168,146 | 9/1979 | Grubb et al. ................. 23/230 B |
| 4,169,014 | 9/1979 | Goldberg ...................... 435/182 |
| 4,200,625 | 4/1980 | Reese ............................. 424/1 |
| 4,347,222 | 8/1982 | Beall et al. .................... 422/211 |
| 4,483,929 | 11/1984 | Szoka ........................... 436/533 |
| 4,496,658 | 1/1985 | Kondo et al. ................. 436/510 |
| 4,499,014 | 2/1985 | Estis ........................... 260/112 R |
| 4,552,812 | 11/1985 | Margel et al. .................. 428/407 |

FOREIGN PATENT DOCUMENTS

| | | |
|---|---|---|
| 0045103A2 | 2/1982 | (EP) . |
| 2523311 | 9/1983 | (FR) . |
| 2086-41A | 5/1982 | (GB) . |
| 2099578A | 12/1982 | (GB) . |

OTHER PUBLICATIONS

Horisberger, "Colloidal Gold: A Cytochemical Marker for Light and Fluorescent Microscopy and for Transmission and Scanning Electron Microscopy" Scanning Electron Microscopy, 11:9–31 (1981).

Goodman, "A Review of the Colloidal Gold Marker System", Scanning Electron Microscopy, 11:133–146 (1980).

Weiser, "The Colloidal Elements" Inorganic Colloid Chemistry, vol. 1, pp. 1–107 (1933).

Glad, Christina & Grubb, Anders O., Immunocapillarymigration–A New Method for Immunochemical Quantitation, Analytical Biochemistry, 1978, 180–187, 85, Academic Press, New York & London.

*Primary Examiner*—Bao-Thuy L. Nguyen

(57) ABSTRACT

Solid phase assay for an analyte wherein binder is supported on a solid support, such as nitrocellulose, and the tracer is comprised of ligand labeled with a colored particulate label, such as a liposome including a dye. The assay has a high sensitivity, and the tracer is visible on the support under assay conditions, whereby tracer can be determined, without instrumentation, and without further treatment thereof.

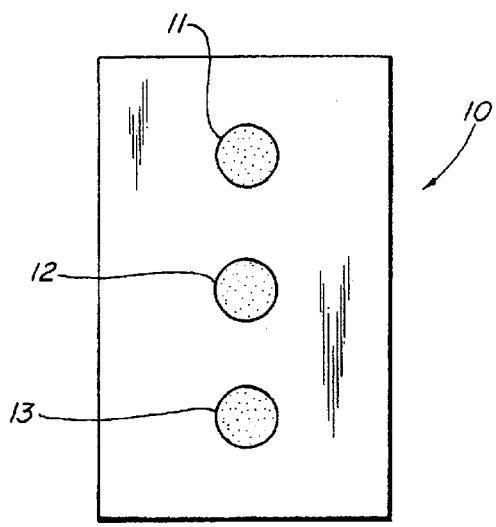

US 4,703,017 C1

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 14, 47, 49 and 62 are determined to be patentable as amended.

Claims 2–13, 15–46, 48 and 50–61, dependent on an amended claim, are determined to be patentable.

New claim 63 is added and determined to be patentable.

1. A process for assaying for an analyte, comprising:

contacting a binder supported on a test area of a solid *support* with a solution of analyte and a tracer, said binder being a binder for at least the analyte, said tracer being comprised of a ligand labeled with a visible particulate label wherein when said particulate label is a sac including a visible dye, said sac is selected from the group consisting of liposomes and microcapsules, said ligand being bound to one of the binder and analyte whereby the tracer is bound to one of the binder on the support and the analyte bound to the binder on the support, said test area being formed of a material having a surface area for supporting the binder and the binder being supported in a concentration whereby bound tracer is visible on the support under assay conditions, said binder being supported in a concentration of at least 1 $\mu g/cm^2$; and determining the visibility of tracer bound in said test area as a measure of analyte in a sample.

14. A process for assaying for an analyte, comprising:

contacting a binder supported on a test area of a solid support with a solution *of* analyte and a tracer, said binder being a binder for at least the analyte, said tracer being comprised of a ligand labeled with a visible particulate label wherein when said particulate label is a sac including a visible dye, said sac is selected from the group consisting of liposomes and microcapsules, said ligand being bound by one of the binder on the support and the analyte bound to the binder on the support, said test area being formed of nitrocellulose, said binder being supported in said test area in a concentration whereby bound tracer is visible on the support under assay conditions, said binder being supported in a concentration of at least 1 $\mu g/cm^2$; and determining the visibility of tracer bound in said test area as a measure of analyte in a sample.

47. The process of claim 1 wherein said test area is capable of supporting binder in a concentration of at least ten micrograms per centimeter *squared*.

49. The process of any one of claims 1 [,] *or* 46 [or 48] wherein the particulate label is a precipitated or insoluble metal or metal alloy.

62. The process of any one of claims 59, 60 or 61 wherein the binder is supported in a concentration of at least 10 [ug/cm] *$\mu g/cm^2$*.

63. *The process of claim 48 wherein the particulate label is a precipitated or insoluble metal or metal alloy.*

* * * * *